(12) United States Patent
Atala et al.

(10) Patent No.: US 11,806,445 B2
(45) Date of Patent: *Nov. 7, 2023

(54) MULTI-LAYER SKIN SUBSTITUTE PRODUCTS AND METHODS OF MAKING AND USING THE SAME

(71) Applicant: Wake Forest University Health Sciences, Winston-Salem, NC (US)

(72) Inventors: Anthony Atala, Winston-Salem, NC (US); Gayoung Jeong, Winston-Salem, NC (US); James J. Yoo, Winston-Salem, NC (US); Sang Jin Lee, Winston-Salem, NC (US); Young-Joon Seol, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 159 days.

This patent is subject to a terminal disclaimer.

(21) Appl. No.: 16/947,053

(22) Filed: Jul. 16, 2020

(65) Prior Publication Data

US 2020/0345899 A1 Nov. 5, 2020

Related U.S. Application Data

(62) Division of application No. 15/542,095, filed as application No. PCT/US2016/012846 on Jan. 11, 2016, now Pat. No. 10,751,448.

(Continued)

(51) Int. Cl.
*A61F 2/10* (2006.01)
*A61L 27/60* (2006.01)

(Continued)

(52) U.S. Cl.
CPC ............ *A61L 27/60* (2013.01); *A61F 2/10* (2013.01); *A61L 27/18* (2013.01); *A61L 27/20* (2013.01);

(Continued)

(58) Field of Classification Search
CPC . A61F 2/10; A61L 27/52; A61L 27/60; A61L 27/3804; A61L 27/273813; A61L 27/3891

(Continued)

(56) References Cited

U.S. PATENT DOCUMENTS

| | | | |
|---|---|---|---|
| 5,727,567 A | | 3/1998 | Carnaby et al. |
| 6,124,273 A | * | 9/2000 | Drohan ............... C08B 37/003 514/8.8 |

(Continued)

FOREIGN PATENT DOCUMENTS

| | | |
|---|---|---|
| EP | 1878790 | 1/2008 |
| FR | 3046420 | 7/2017 |

(Continued)

OTHER PUBLICATIONS

English translation KR-10-2008-0007183 Epidermis Equivalent Capable of Pigmenting Obtained from Matrix Cells Method of Preparation and Use (Year: 2007).*

(Continued)

*Primary Examiner* — Suzette J Gherbi
(74) *Attorney, Agent, or Firm* — Myers Bigel, P.A.

(57) ABSTRACT

Provided are live, artificial, skin substitute products and methods of making and using the same, such as for wound treatment and compound testing, including compound testing for efficacy, toxicity, penetration, irritation and/or metabolism testing of drug candidates or compositions such as cosmetics.

18 Claims, 6 Drawing Sheets

CELL VIABILITY (LIVE/DEAD): T=3 DAYS IMMERSION CULTURE, 3 MILLION/mL

Related U.S. Application Data

(60) Provisional application No. 62/242,008, filed on Oct. 15, 2015, provisional application No. 62/102,154, filed on Jan. 12, 2015.

(51) Int. Cl.

| | | |
|---|---|---|
| *B33Y 80/00* | (2015.01) | |
| *B33Y 70/00* | (2020.01) | |
| *C08L 5/08* | (2006.01) | |
| *A61L 27/20* | (2006.01) | |
| *C08L 89/06* | (2006.01) | |
| *C12N 5/071* | (2010.01) | |
| *B29C 64/106* | (2017.01) | |
| *B33Y 10/00* | (2015.01) | |
| *A61L 27/18* | (2006.01) | |
| *A61L 27/38* | (2006.01) | |
| *A61L 27/52* | (2006.01) | |
| *G01N 33/50* | (2006.01) | |
| *B29K 75/00* | (2006.01) | |
| *B29K 105/00* | (2006.01) | |

(52) U.S. Cl.
CPC ....... *A61L 27/3804* (2013.01); *A61L 27/3813* (2013.01); *A61L 27/3839* (2013.01); *A61L 27/3891* (2013.01); *A61L 27/52* (2013.01); *B29C 64/106* (2017.08); *B33Y 10/00* (2014.12); *B33Y 70/00* (2014.12); *B33Y 80/00* (2014.12); *C08L 5/08* (2013.01); *C08L 89/06* (2013.01); *C12N 5/0698* (2013.01); *G01N 33/502* (2013.01); *G01N 33/5044* (2013.01); *A61F 2210/0076* (2013.01); *A61F 2240/001* (2013.01); *A61L 2300/64* (2013.01); *A61L 2430/34* (2013.01); *B29K 2075/00* (2013.01); *B29K 2105/0061* (2013.01); *C12N 2502/091* (2013.01); *C12N 2502/092* (2013.01); *C12N 2502/094* (2013.01); *C12N 2502/1305* (2013.01); *C12N 2502/1323* (2013.01); *C12N 2533/30* (2013.01); *C12N 2533/54* (2013.01); *C12N 2533/80* (2013.01)

(58) Field of Classification Search
USPC .......................................................... 623/10
See application file for complete search history.

(56) References Cited

U.S. PATENT DOCUMENTS

| | | | | |
|---|---|---|---|---|
| 6,428,802 | B1 | 8/2002 | Atala | |
| 6,482,231 | B1* | 11/2002 | Abatangelo | A61L 27/3895 623/11.11 |
| 7,928,069 | B2 | 4/2011 | Prestwich | A61K 47/61 530/356 |
| 10,751,448 | B2* | 8/2020 | Atala | A61L 27/3813 |
| 11,266,344 | B2* | 3/2022 | Kim | A61B 5/443 |
| 2003/0232746 | A1* | 12/2003 | Lamberti | A61K 47/42 514/59 |
| 2008/0097607 | A1 | 4/2008 | Bakkar et al. | |
| 2009/0004276 | A1* | 1/2009 | Ben-Shalom | A61K 9/06 514/777 |
| 2009/0208466 | A1 | 8/2009 | Yoo et al. | |
| 2012/0089238 | A1 | 4/2012 | Kang et al. | |
| 2012/0276154 | A1 | 11/2012 | Mahjour et al. | |
| 2014/0112973 | A1 | 4/2014 | Steinberg et al. | |
| 2016/0122723 | A1* | 5/2016 | Retting | A61L 27/60 435/395 |
| 2016/0243286 | A1* | 8/2016 | Collins | A61L 27/3834 |
| 2018/0117087 | A1* | 5/2018 | Zhang | A61K 35/22 |
| 2018/0272035 | A1* | 9/2018 | Retting | A61L 27/362 |
| 2018/0346873 | A1* | 12/2018 | Marquez | A61K 35/39 |
| 2021/0212810 | A1* | 7/2021 | Varkey | A61F 2/105 |
| 2021/0282703 | A1* | 9/2021 | Kim | A61B 5/688 |
| 2022/0202727 | A1* | 6/2022 | Shin | C12N 11/10 |

FOREIGN PATENT DOCUMENTS

| | | | |
|---|---|---|---|
| FR | 3046420 A1 * | 7/2017 | ......... A61L 27/3843 |
| JP | H10118103 | 5/1998 | |
| JP | 2000508922 | 7/2000 | |
| JP | 2005132813 | 5/2005 | |
| JP | 2005305177 | 11/2005 | |
| JP | 2009011588 | 1/2009 | |
| JP | 2012235921 | 12/2012 | |
| KR | 10-2008-0007183 A | 1/2008 | |
| KR | 10-2014-0023300 A | 2/2014 | |
| WO | 2007/124023 | 11/2007 | |
| WO | 2012/122105 | 9/2012 | |
| WO | 2012/153815 | 11/2012 | |
| WO | 2014/179559 | 11/2014 | |
| WO | 2014/186430 | 11/2014 | |
| WO | 2016/115034 | 7/2016 | |

OTHER PUBLICATIONS

English Translation KR-10-2014-002330 Delivery System (Year: 2014).*
European Examination Report corresponding to EP 16737671.4; dated Dec. 9, 2021 (5 pages).
Canadian Office Action corresponding to CA 2,972,094; dated Mar. 28, 2022 (5 pages).
European Examination Report corresponding to EP 16737671.4; dated Sep. 8, 2020 (6 pages).
Kato et al. "Allogeneic Transplantation of an Adipose-Derived Stem Cell Sheet Combined With Artificial Skin Accelerates Wound Healing in a Rat Wound Model of Type 2 Diabetes and Obesity" Diabetes, 64(8): 2723-2734 (Aug. 2015).
Australian Examination Report corresponding to Australian Patent Application No. 2016206994 (dated Sep. 4, 2019) (4 pp).
Australian Examination Report corresponding to Australian Patent Application No. 2016206994, dated Jan. 6, 2020 (4 pp).
Bellas et al. "In Vitro 3D full thickness skin equivalent tissue model using silk and collagen biomaterials" Macromol Biosci., 12(12):1627-1636 (2012).
Brohem Ca et al. Artificial skin in perspective: concepts and applications. Pigment Ceii Melanoma Res. 201024: 35-50.
European Examination Report corresponding to EP16737671.4 (dated Jul. 30, 2019) (8 pp).
European Search Report and Opinion, EP76737671, dated Jul. 18, 2018, 12 pages.
International Search Report and Written Opinion, PCT/US2016/012846, dated Mar. 16, 2016.
Japanese Office Action corresponding to JP 2017-536836, dated Feb. 4, 2020 (7 pages, including English translation).
LEE et al. "Design and Fabrication of Human Skin by Three-Dimensional Bioprinting" Tissue Engineering: Part C, 20(6):473-484 (2014).
Monfort et al. "Production of human tissue-engineered skin trilayer on a plasma-based hypodermis" Journal of Tissue Engineering and Regenerative Medicine, 7(6):479-490 (2013).
Skardal et al. "Bioprinted Amniotic Fluid-Derived Stem Cells Accelerate Healing of Large Skin Wounds" Stem Cells Translational Medicine, 1(11):792-802 (2012).
Sugihara et al. "Effects of fat ceils on keratinocytes and fibroblasts in a reconstructed rat skin model using collagen gel matrix culture" British J Dermatology, 144(2):244-253 (2001). Abstract.
Korean Office Action corresponding to KR 10-2017-7020749, dated Aug. 25, 2022 (24 pages, including English machine translation).
Canadian Office Action corresponding to CA 2,972,094; dated Dec. 2, 2022 (4 pages).

(56) References Cited

OTHER PUBLICATIONS

Korean Decision of Rejection corresponding to KR 10-2017-7020749, dated Feb. 23, 2023 (8 pages, Including English translation).

* cited by examiner

MULTI-LAYER SKIN SUBSTITUTE PRODUCTS AND METHODS OF MAKING AND USING THE SAME

RELATED APPLICATIONS

This application is a divisional application of U.S. patent application Ser. No. 15/542,095, filed Jul. 7, 2017, now allowed, which is a 35 U.S.C. § 371 national phase entry of PCT Application PCT/US2016/012846, filed Jan. 11, 2016, and published in English on Jul. 21, 2016, as International Publication No. WO 2016/115034, and which claims the benefit of U.S. Provisional Patent Application Ser. No. 62/102,154, filed Jan. 12, 2015, and U.S. Provisional Patent Application Ser. No. 62/242,008, filed Oct. 15, 2015, the disclosure of each of which is incorporated by reference herein in its entirety.

FIELD OF THE INVENTION

The present invention concerns live, artificial, skin substitute products and methods of making and using the same, such as for wound treatment and compound testing.

BACKGROUND OF THE INVENTION

The current "gold standard" for skin replacement is the use of autologous skin grafts. However, due to donor-site tissue availability, complex maintenance and costs of such tissues, this treatment is often limited for patients. Also, most current engineered skins or skin substitutes do not fully recapitulate native skin as they are devoid of multiple skin cell types and structures like trilayers and dermal appendages. The current commercially available skin cellular models are also limited as they only use either immortalized cell lines derived from skin tumors or one or two primary cell types (e.g., keratinocytes and/or dermal fibroblasts) to be simple; thus they do not well represent and replicate the complexity of in vivo skin.

E. Bellas et al., In vitro 3D full thickness skin equivalent tissue model using silk and collagen biomaterials, *Macromol. Biosci* 12, 1627-1636 (2012), utilize adipose derived stem cells, keratinocytes, and fibroblasts to created a tri-layer skin-like product, but require the use of a silk scaffold onto which cells are seeded.

A. Skardal et al., Bioprinted Amniotic Fluid-Derived Stem Cells Accelerate Healing of Large Skin Wounds, *Stem Cells Translational Medicine* 1, 792-802 (2012), describes bioprinting of a skin-substitute directly onto a large wound, but use only amniotic fluid stem cells and bone-marrow-derived mesenchymal stem cells.

A. Monfort et al., Production of a human tissue-engineered skin trilayer on a plasma-based hypodermis, *J. Tissue Eng. Regen. Med.* 7, 479-490 (2013), describes a skin-like trilayer product, but employed only adipogenic cells, fibroblasts, and keratinocytes, and used sequential culturing techniques that required 35 days to complete. Id. at 480-81.

V. Lee et al., Design and Fabrication of Human Skin by Three-Dimensional Bioprinting, *Tissue Engineering* 20, 473-484 (2014), describe a skin-like product, created with 3D bioprinting, but utilize only keratinocytes and fibroblasts, printed between separate collagen layers. See, e.g., FIG. 2 therein.

Based on the foregoing, there remains a need for improved skin substitute products that can be used for therapeutic, and drug testing, purposes.

SUMMARY OF THE INVENTION

Described herein is an artificial mammalian skin substitute product, comprising:

(a) optionally, but in some embodiments preferably, a first ("hypodermis-like") layer comprising live mammalian adipocytes (e.g., induced pre-adipocytes) in a first hydrogel carrier;

(b) a second ("dermis-like") layer contacting or directly contacting the first layer and comprising live mammalian fibroblast cells and live mammalian follicle dermal papilla cells in combination in a second hydrogel carrier;

(c) a third ("epidermis-like") layer contacting or directly contacting the second layer (i.e., on the opposite side thereof as the first layer, so that the second layer is sandwiched between the first and third layers when the first layer is present), the third layer comprising live mammalian keratinocytes and live mammalian melanocytes in combination in a third hydrogel carrier.

In some embodiments, the first, second, and/or third hydrogel carriers comprise cross-linked hyaluronic acid, and/or the second and/or third hydrogel carriers optionally but preferably further comprise collagen.

In some embodiments, the second and third layers are at least partially cross-linked with one another (either directly, or through an intervening cross-linkable layer).

In some embodiments, the first layer is present and the first and second layers are at least partially cross-linked with one another.

In some embodiments:
(i) the first layer, when present, has a thickness of from 100, 200 or 300 micrometers up to 400, 600 or 800 micrometers;
(ii) the second layer has a thickness of from 100, 200 or 300 micrometers up to 400, 600 or 800 micrometers;
(iii) the third layer has a thickness of from 100, 200 or 300 micrometers up to 400, 600 or 800 micrometers; and/or
(iv) the product has a total thickness of from about 200, 400 or 600 micrometers up to 800, 1200 or 1600 micrometers when said first layer is absent, or a total thickness of 300, 600 or 900 micrometers up to 1200, 1800 or 2400 micrometers when said first layer is present.

In some embodiments, each of the first layer when present, the second layer, and the third layer have overlying surface areas of from 0.5, 1 or 10 square centimeters up to 50, 200 or 400 square centimeters, or more.

In some embodiments:
(i) the adipocytes are included in said first hydrogel carrier in an amount of from 1 or 2 million to 8, 10, 15 or 20 million (preferably 4 to 6 million or 10 to 20 million) cells per cubic centimeter; and/or
(ii) the fibroblast cells and the dermal papilla cells are included in the second hydrogel carrier in a ratio of about 8:1 or 6:1 to 2:1 or 1:1 (preferably 5:1 to 3:1) and/or at a combined density of about 5 or 8 million to 15, 20, 25 or 30 million (preferably about 10 million or about 20-25 million) cells per cubic centimeter; and/or
(iii) the keratinocytes and melanocytes are included in the third hydrogel carrier in a ratio of about 20:1 or 10:1 to 8:1, 5:1, 3:1 or 2:1 (preferably from 12:1 to 3:1) and/or at a combined density of about 5 or 8 million to 15, 20, 25, 30 or 35 million (preferably about 10 million or about 20-30 million) cells per cubic centimeter.

In some embodiments, the live mammalian adipocytes are human adipocytes; said live mammalian fibroblast cells are human fibroblast cells, said live mammalian follicle dermal papilla cells are human follicle dermal papilla cells, said live mammalian keratinocytes are human keratinocytes, and said live mammalian melanocytes are human melanocytes.

Some embodiments further comprise antigen-presenting dendritic cells or precursors thereof between the first layer and the second layer, in the second layer, between the second layer and the third layer, and/or in said third layer (e.g., in a total amount of from 1 or 2 million to 8 or 10 million (preferably 4 to 6 million) cells per cubic centimeter).

Some embodiments further comprise neural cells or precursors thereof between said first layer and said second layer, in said second layer, between said second layer and said third layer, and/or in said third layer (e.g., in a total amount of from 1 or 2 million to 8 or 10 million (preferably 4 to 6 million) cells per cubic centimeter).

Methods of making and using the foregoing, for wound treatment and compound or composition screening, are also disclosed herein.

Yoo, Xu and Atala et al., US Patent Application Publication No. US 2009/0208466 (August 2009) suggests skin substitute products at page 3, paragraphs 0037-0041, but, among other differences from the inventions described herein, does not suggest or describe how papilla cells may be effectively incorporated therein, do not suggest that different layers be at least partially crosslinked with one another, and (contrary to the organization described herein) suggest that adipocytes and fibroblasts be incorporated together in the same "dermal" layer.

The present invention is explained in greater detail in the drawings herein and the specification set forth below.

Figure 1:
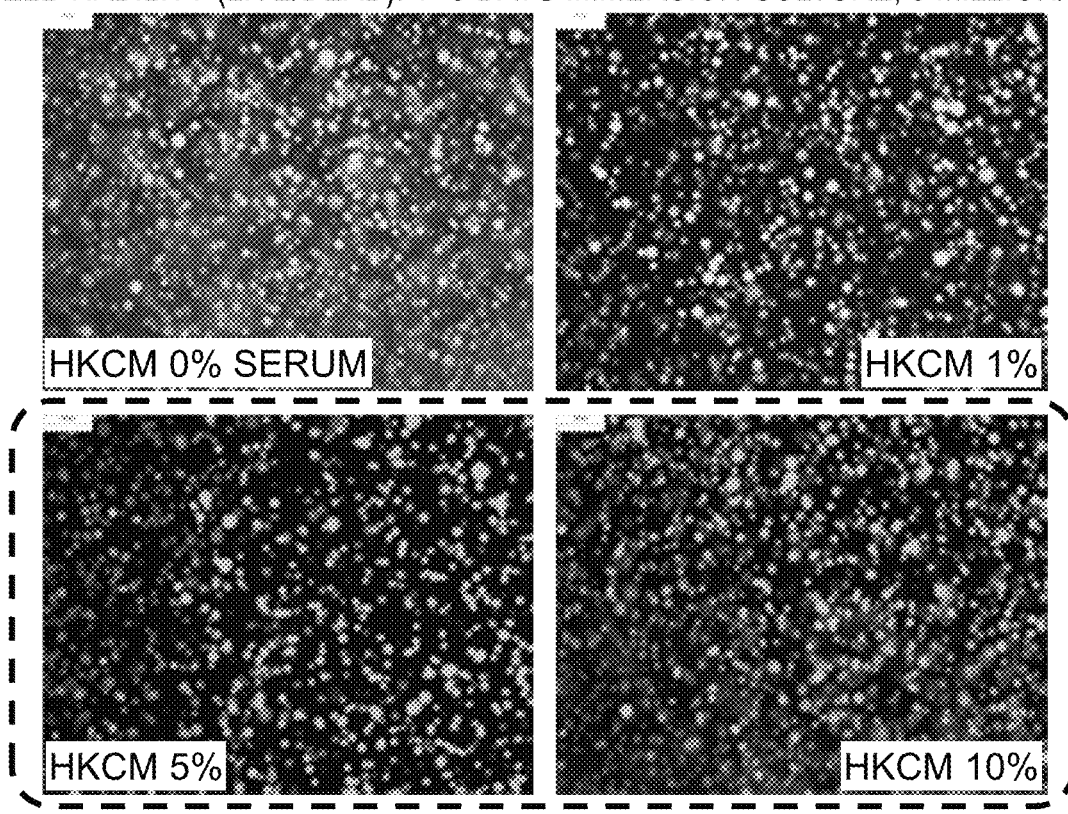
FIG. 1: Effects of serum level on the cell viability (3D).

The present invention is explained in greater detail in the drawings herein and the specification set forth below. The disclosures of all United States patent references cited herein are incorporated by reference herein in their entireties.

DETAILED DESCRIPTION OF ILLUSTRATIVE EMBODIMENTS

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section.

"Mammalian" as used herein refers to both human subjects (and cells sources) and non-human subjects (and cell sources or types), such as dog, cat, mouse, monkey, etc. (e.g., for veterinary or research purposes).

"Hydrogel" as used herein may be any suitable hydrogel. In general, the hydrogel includes water and is further comprised of or derived from polyalkylene oxides, poloxamines, celluloses, hydroxyalkylated celluloses, polypeptides, polysaccharides, carbohydrates, proteins, copolymers thereof, or combinations thereof, and more particularly are comprised of or derived from poly(ethylene glycol), poly(ethylene oxide), poly(vinyl alcohol), poly(vinylpyrrolidone), poly(ethyloxazoline), poly(ethylene oxide)-co-polypropylene oxide) block copolymers, carboxymethyl cellulose, hydroxyethyl cellulose, methylhydroxypropyl cellulose, polysucrose, hyaluronic acid, dextran, heparan sulfate, chondroitin sulfate, heparin, alginate, gelatin, collagen, albumin, ovalbumin, copolymers thereof, and combinations thereof, all of which are preferably cross-linked to varying degrees in accordance with known techniques, or variations thereof that are apparent to those skilled in the art. See, e.g., U.S. Pat. Nos. 8,815,277; 8,808,730; 8,754,564; 8,691,279. In some embodiments, a cross-linked hyaluronic acid hydrogel (optionally including additional polymers such as gelatin) is preferred.

Antigen presenting dendritic cells, including precursors thereof (e.g., induced or differentiated embryonic stem cells; CD34+ bone marrow precursor cells) are known. See, e.g., U.S. Pat. Nos. 6,008,004 and 8,785,189.

Neural stem cells, including precursors thereof, are known. See, e.g., U.S. Pat. Nos. 6,001,654 and 8,785,187.

Vascular cells, including precursors thereof and cells that can self-organize into a vascular network, are known. See, e.g., US Patent Application Publication Nos. US 20140273220 and US20140201988.

1. Skin Substitute Products and Methods of Making the Same.

Products of the invention may be made by the steps of:

(a) optionally depositing a first ("hypodermis-like") layer comprising live mammalian adipocytes (e.g., induced preadipocytes) in a first hydrogel carrier on a substrate (e.g., an inert substrate such as a porous polymer mesh; collagen, etc.; or a wound on a subject in need of treatment); then (preferably within one half hour or less);

(b) depositing a second ("dermis-like") layer on said first layer when present (or on said substrate when said first layer is not present), said second layer comprising live mammalian fibroblast cells and live mammalian follicle dermal papilla cells in a second hydrogel carrier; and then (preferably within one half hour or less);

(c) depositing a third ("epidermis-like") layer on said second layer, said third layer comprising live mammalian keratinocytes and live mammalian melanocytes in a third hydrogel carrier.

In some embodiments, the first hydrogel carrier, when deposited, is deposited in prepolymerized or partially polymerized form; the second hydrogel carrier is deposited in prepolymerized or partially polymerized form; and/or the third hydrogel carrier is deposited in prepolymerized or partially polymerized form.

In some embodiments, the depositing steps (a) and (b) are carried out under conditions in which said first hydrogel in said first layer, when present, and said second hydrogel in said second layer at least partially crosslink with one another; and said depositing steps (b) and (c) are carried out under conditions in which said second hydrogel in said second layer and said third hydrogel in said third layer at least partially crosslink with one another. The layers may be crosslinked directly, or through an intervening cross-linkable layer.

In some embodiments, the first, second, and/or third hydrogel carriers comprise cross-linked hyaluronic acid, and/or the second and/or third hydrogel carriers optionally but preferably further comprise collagen.

In some embodiments, the depositing is carried out under conditions in which the second and third layers are at least partially cross-linked with one another, and/or the first layer and second layers are at least partially cross-linked with one another typically by carrying out the depositing steps sufficiently close in time so that cross-linking reaction between the two layers may occur.

In some embodiments, partial or complete intervening layer(s), e.g., intervening hydrogel layer(s), can be interposed between the first and second hydrogen layers, and/or the second and third hydrogel layers, with the first and second, and/or second and third, hydrogel layers optionally cross-linked with their respective intervening hydrogel layer(s). By "partial" intervening layer is meant that the layer has openings therein through which the first and second, and/or second and third, layers directly contact one another. In addition, additional cell types such as described below may optionally be deposited with such intervening layers. The hydrogels of these intervening layer(s), when present, may be formed of the same materials as the first, second, and/or third hydrogel layers, and like those layers may be deposited in partially crosslinked form.

In some embodiments: (i) said first layer, when present, has a thickness of from 100, 200 or 300 micrometers up to 400, 600 or 800 micrometers; (ii) said second layer has a thickness of from 100, 200 or 300 micrometers up to 400, 600 or 800 micrometers; (iii) said third layer has a thickness of from 100, 200 or 300 micrometers up to 400, 600 or 800 micrometers; and/or (iv) said product has a total thickness of from about 200, 400 or 600 micrometers up to 800, 1200 or 1600 micrometers when said first layer is absent, or a total thickness of 300, 600 or 900 micrometers up to 1200, 1800 or 2400 micrometers when said first layer is present.

In some embodiments, each of the first layer when present, said second layer, and said third layer have overlying surface areas of from 0.5, 1 or 10 square centimeters up to 50, 200 or 400 square centimeters.

Cells may be included in any suitable amount. In some embodiments: (i) said adipocytes are included in said first hydrogel carrier in an amount of from 1 or 2 million to 8, 10, 15 or 20 million (preferably 4 to 6 million or 10 to 20 million) cells per cubic centimeter; and/or (ii) said fibroblast cells and said dermal papilla cells included in said second hydrogel carrier in a ratio of about 8:1 or 6:1 to 2:1 or 1:1 (preferably 5:1 to 3:1) and/or at a combined density of about 5 or 8 million to 15, 20, 25 or 30 million (preferably about 10 million or about 20-25 million) cells per cubic centimeter; and/or (iii) said keratinocytes and said melanocytes included in said third hydrogel carrier in a ratio of about 20:1 or 10:1 to 8:1, 5:1, 3:1 or 2:1 (preferably from 12:1 to 3:1) and/or at a combined density of about 5 or 8 million to 15, 20, 25, 30 or 35 million (preferably about 10 million or about 20-30 million) cells per cubic centimeter.

Cells may be obtained from established cultures, donors, or a combination thereof. In some embodiments, said live mammalian adipocytes are human adipocytes; said live mammalian fibroblast cells are human fibroblast cells, said live mammalian follicle dermal papilla cells are human follicle dermal papilla cells, said live mammalian keratinocytes are human keratinocytes, and/or said live mammalian melanocytes are human melanocytes.

A variety of additional enhancements may be made to the foregoing. For example, in some embodiments, the method may further comprise depositing antigen-presenting dendritic cells or precursors thereof between said first layer and said second layer, in said second layer, between said second layer and said third layer, and/or in said third layer (e.g., in a total amount of from 1 or 2 million to 8 or 10 million (preferably 4 to 6 million) cells per cubic centimeter).

In some embodiments, the method may further comprise depositing neural cells or precursors thereof between said first layer and said second layer, in said second layer, between said second layer and said third layer, and/or in said third layer (e.g., in a total amount of from 1 or 2 million to 8 or 10 million (preferably 4 to 6 million) cells per cubic centimeter).

In some embodiments, the method may further comprise depositing vascular cells or precursors thereof between said first layer and said second layer, in said second layer, between said second layer and said third layer, and/or in said third layer (e.g., in a total amount of from 1 or 2 million to 8 or 10 million (preferably 4 to 6 million) cells per cubic centimeter).

In some embodiments, the construct has a diameter or width of from 1 to 5 millimeters, or from 3 to 7 millimeters, or from 5 to 10 millimeters, or from 8 to 16 millimeters, or from 10 to 20 millimeters, or from 20 to 50 millimeters, or from 30 to 80 millimeter, or from 50 to 100 millimeters.

Depositing can be carried out by any suitable technique, including but not limited to spraying, spreading/painting, coating, etc. In some preferred embodiments the depositing steps are carried out by printing or bioprinting in accordance with any suitable technique, including both "ink jet" type printing and syringe injection type printing. Apparatus for carrying out such bioprinting is known and described in, for example, Boland et al., U.S. Pat. No. 7,051,654; Yoo et al., US Patent Application Pub. No. US 2009/0208466; and Kang et al., US Patent Application Publication No. US 2012/0089238.

When deposited on an inert substrate, the products described above may be removed therefrom and used immediately, or maintained and further propagated on that support in vitro in any suitable culture media. The products may be packaged (with or without the support, or transferred to a different support) in a sterile container or package for subsequent use if desired, along with appropriate nutrients and/or culture media.

The support may be porous or non-porous. For example, the support may be a porous filter, membrane or mesh that is permeable to media nutrients for diffusion to the live cells of the construct, e.g., of one or more of the layers.

2. Methods of Use in Wound Treatment.

A wound, such as a burn, incision (including surgical incision), abrasion, laceration or the like on a subject may be treated by topically applying a skin substitute product as described herein to that wound in a treatment-effective configuration (e.g., sufficiently covering or overlying the wound to aid in the healing thereof). Depending on the nature of the wound, such as a burn which is not deep, the first "hypodermis-like" layer may not be required. Suitable subjects include both human subjects, and other animal (typically mammalian) subjects (e.g., dogs, cats, cows, pigs, sheep, horses, etc.) for veterinary (including veterinary medicine and pharmaceutical screening) purposes.

In some embodiments, the wound may be a facial wound, such as a wound of the forehead, glabella, nasion, nose (e.g., nasal bridge, rhinion, infatip lobule, supratip, columella, alar-sidewall), nasolabial fold, philtrum, lips, chin, cheek, jaw, ear (e.g., helix, scapha, antihelical fold, antihelix, antitragus, lobule, tragus, concha, fossa), skin surrounding the eye (e.g., eyelid), etc.

In some embodiments, the live skin product may be fabricated on a customized mold made of an inert substrate in order to provide a personalized shape for wound healing. The mold may be fabricated based on clinical image data such as CT data, optionally modified to impart the desired shape and features for the wound healing. As a nonlimiting example, the mold may be formed from a polymeric material (e.g., polyurethane), optionally dispensed from a printer as taught herein. In some embodiments, the wound may be the result of a surgery or other medical procedure, such as plastic surgery.

In some embodiments, an epidermis layer is deposited on the inert substrate, a dermis layer is deposited on the epidermis layer, and optionally a hypodermis layer is deposited on the dermis layer (depending on the nature of the wound and the need for the hypodermis in the wound treatment).

In some embodiments, the live skin product comprising an inert substrate layer is molded to snugly fit onto the complex contour, shape and architecture of facial wounds.

In some embodiments, one or more cell types of the product are autologous with respect to the subject to be treated. In some embodiments, one or more cell types of the product are allogenic with respect to the subject to be treated.

3. Methods of Use in Compound Testing.

Live skin substitute products as described herein may be used as an alternative to live animal testing for compound or composition screening (e.g., screening for efficacy, toxicity, penetration, irritation, or other metabolic or physiological activity). Such testing may be carried out by providing a skin substitute product as described herein under conditions which maintain constituent cells of that product alive (e.g., in a culture media with oxygenation); applying a compound or composition to be tested (e.g., a drug candidate, typically provided in a vehicle or carrier, a topical composition such as a soap or cosmetic, etc.) to that product (e.g., by topical application to said third layer); and then detecting a physiological response (e.g., damage, scar tissue formation, irritation, penetration, cell proliferation, etc.) to said skin substitute product (e.g., burn, cell death, marker release such as histamine release, cytokine release, changes in gene expression, etc.), the presence of such a physiological response indicating said compound or composition has therapeutic efficacy, toxicity, irriation, pentration, or other metabolic or physiological activity if applied to the skin of a mammalian subject. A control sample of the skin substituted may be maintained under like conditions, to which a control compound or composition (e.g., physiological saline, compound vehicle or carrier) may be applied, so that a comparative result is achieved, or damage can be determined based on comparison to historic data, or comparison to data obtained by application of dilute levels of the test compound or composition, etc.

In some embodiments, the live skin substitute construct is form on and/or provided on an insert configured to be placed into a cell culture dish (e.g., a petri dish, a 2-well plate, a 6-well plate, a 12-well plate, a 24-well plate, 48-well plate, 96-well plate, etc.), such as a cell culture insert. Cell culture inserts are known and described in, e.g., U.S. Pat. Nos. 5,652,142, 5,578,492, 5,468,638, 5,470,473, etc.

The present invention is explained in greater detail in the following non-limiting Examples.

EXAMPLES

Fabrication of Bioprinted Skin Substitutes In Vitro

In this example, pilot studies for optimizing culture conditions for 3D reconstructed or bioprinted in vitro skin substitutes with five human primary skin cells seeded with hyaluronan-gelatin based polyethylene glycol (PEG) hydrogels are presented.

Objectives of these Examples are: [1] To test and compare the viability and proliferation of cells seeded within gels with different media conditions (0, 1, 5, & 10% serum level); [2] To test the feasibility of encapsulating 5 different skin cells within hydrogels with even distribution and to determine an appropriate cell density per construct; and [3] To show the feasibility of bioprinting trilayered 3D skin constructs in vitro with nice layering and cell presentation.

Cell Sources. Human adult keratinocytes (K), melanocytes (Mel), dermal fibroblasts (DF), follicle dermal papilla cells (FDPC), and pre-adipocytes (p-Ad) and related growth media (GM) and differentiation media (DM) were purchased from Promocell (Heidelberg, Germany) and Life Technologies (Calsbad, Calif., USA). All cells used for bioprinting were pooled from N=3-4 donors (P3-P8). For epidermis, the ratio between keratinocytes and melanocytes was kept to be 9:1 and the cell density was kept at 10 million cells/ml. For dermis, the ratio between dermal fibroblasts and follicle dermal papilla cells was kept to be 4:1 and the cell density was also kept at 10 million cells/ml. For hypodermis, pre-adipocytes were pre-cultured and induced in monolayer for 2-3 days with pre-standardized differentiation media (Promocell, Germany) and induced adipocytes (iAd) were used to print at 5 million cells/ml.

Hydrogel Preparation. Commercially available hyaluronic acid-gelatin based hydrogels (HyStem®-C, ESI-BIO, Alameda, Calif.) were used as the 'biopaper.' More specifically, 1% thiolated hyaluronic-acid (Glycosil)-1% thiolated gelatin (Gelin-S) with 2-4% PEGDA (Extralink) or 4-arm-PEGA (Creative PEGworks, Winston Salem, N.C., USA) were used as crosslinking agents for various gelation time and stiffness. Also, human collagen (10-20% (v/v), 3 mg/ml, ESI-BIO) solution was added for dermis and epidermis layers when making hydrogels.

3D Printing. A customized 3D bioprinter (A. Skardal et al., Bioprinted Amniotic Fluid-Derived Stem Cells Accelerate Healing of Large Skin Wounds, *Stem Cells Translational Medicine* 1, 792-802 (2012)) was used. Cells and mixed cells and hydrogels ('bioink' and 'biopaper') were loaded into a sterile syringe for each different layer to print. 300 μm sized nozzle and 20-80 kPa pressures were used depending on viscosity of each hydrogel, and cell/gel solution was printed according to an evenly-spaced, coil-shaped pattern at various scan speeds. In general, 6-8 constructs were printed per a syringe loading. Cell/gel solution was printed on top of the polycarbonate transwell filter (Millipore, D=12 mm) after cell free hydrogel coating and each layer was made sure to be completely gelled before printing next layer. In general, each layer was 300-350 μm. Thus, the entire trilayered structures were about 900-1200 μm in thicknesses.

After printing, each skin construct printed inside the insert was placed in a 6-well plate, and was cultured with 5% heat inactivated serum keratinocyte based media (5% HKM, Promocell, Germany). For immersion culture, 300-400 μl and 2.5-3 ml of 5% HKM for inside and outside of the inserts were used, respectively, and media was changed every other day. The bioprinted skin constructs were cultured in a standard cell culture incubator with constant temperature at 37° C. and 5% $CO_2$.

Assessments. Histology (H&E, Mason Trichrome), Immunohistochemistry (IHC), 2D and 3D confocal/microscopic images of pre-labelled cells (Qtrackers) for migration and viability (Live/Dead), and MTS assay.

Results. The effects of serum level on the cell viability (3D) are shown in FIG. 1. Serum free KGM2 media (Promocell) showed the lowest cell viability and 5% and 10% serum added KGM2 media seemed to be comparable to each other and most optimal in terms of cell viability qualitatively. The qualitative results from Live/Dead were confirmed by two times of MTS cell viability assays: [1] five skin cells intermixed within hydrogels and [2] individual skin cell encapsulated within hydrogels.

Figure 2:
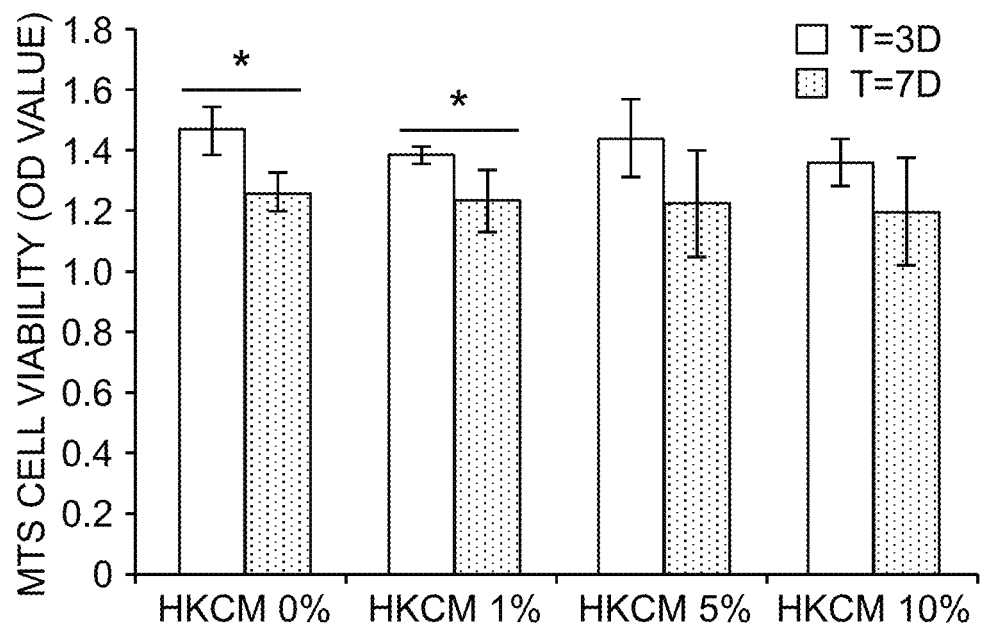
FIG. 2: Five skin cells intermixed within a hydrogel construct (N=4).

FIG. 2 reports on five skin cells intermixed within a hydrogel construct (N=4). No significant difference among different serum levels at the same time quantitatively was found. Serum free and 1% serum-keratinocytes media probably do not support other cells' growth sufficiently over time.

Figure 3:
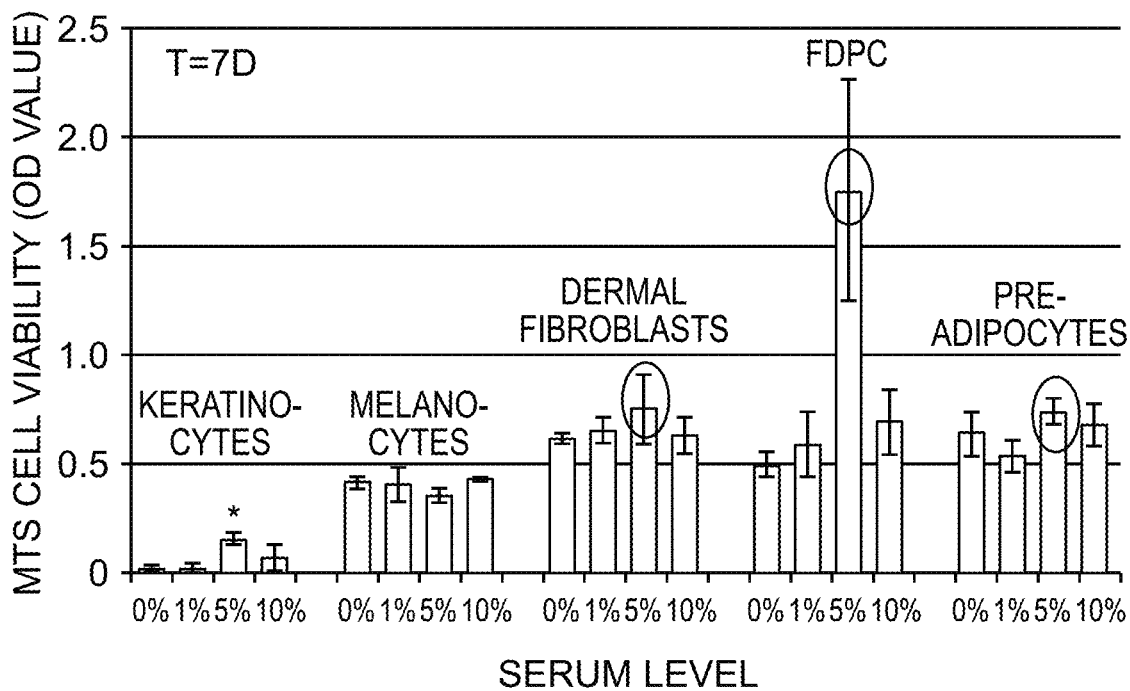
FIG. 3: Individual skin cell encapsulated within hydrogels (N=4).

FIG. 3 reports on individual skin cell encapsulated within hydrogels (N=4). Keratinocytes proliferated the most at 5% serum level significantly. 5% serum level media showed the highest proliferation for all skin cell types except melanocytes. Regardless of serum conditions, keratinocytes showed the lowest proliferation compared to other skin cell types.

Figure 4:
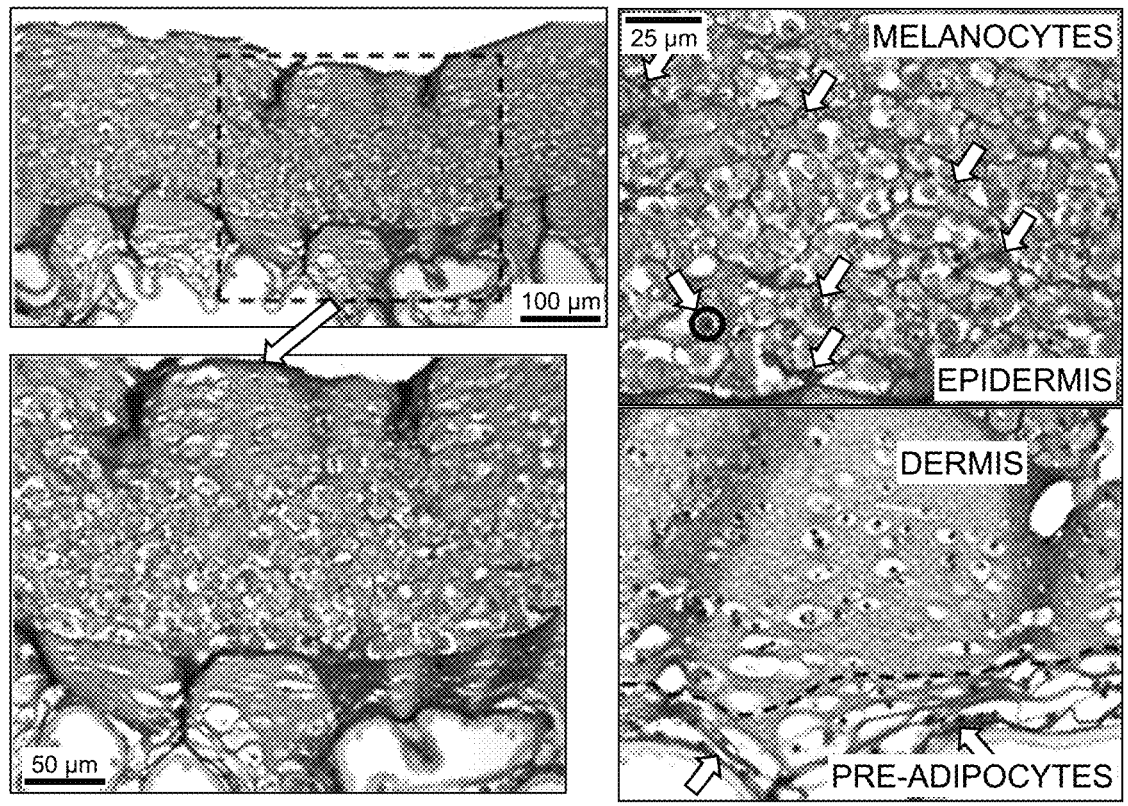
FIG. 4: Bioprinted skin substitute construct in vitro (t=6d, 10-5-5 million/layer (top to bottom)).

FIG. 4 shows a bioprinted skin substitute construct in vitro (t=6d, 10-5-5 million/layer (top to bottom)). Bioprinting of trilayered 3D in vitro skin constructs (epidermis: keratinocytes+melanocytes; dermis: dermal fibroblasts+follicle dermal papilla cells; hypodermis: pre-adipocytes) with well-positioned cells in each layer was successfully done; we could observe clear distinctions between layers, and the presence of trilayers with each specific cell type that we printed. Each cell phenotype seemed to be well-maintained up to 6 days of culture.

Figure 5:
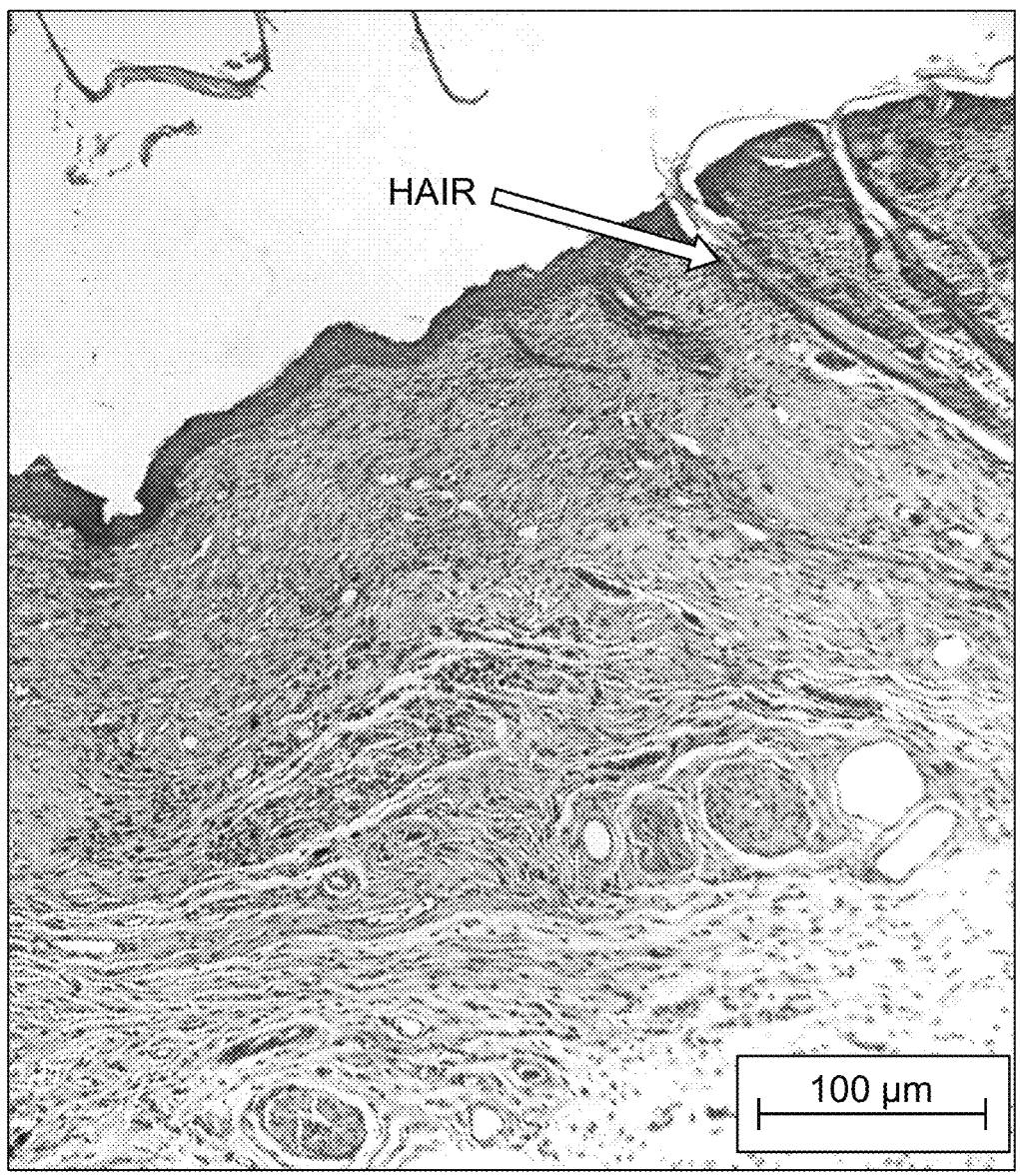
FIG. 5: Hair growth in bioprinted skin substitute construct after 3 weeks of growth in vitro.

FIG. 5 shows a bioprinted skin substitute construct similar to that of FIG. 4, three weeks after topical implantation onto a mouse, with a hair follicle formed therein and a hair growing from that follicle.

Conclusions. It is feasible to encapsulate 5 different primary skin cells within hyaluronan-based hydrogels via hand-seeding and bioprinting. Unlike single cell culture of keratinocytes in vitro, among testing conditions, at least 5% serum level is necessary for maintaining cell viability for multiple skin cell co-culture in vitro. Based on both Live/Dead and MTS assays, 5% serum level keratinocytes growth medium would be used for the in vitro culture of 5 skin cells after printing.

Further Fabrication of Bioprinted Skin Substitutes In Vitro

Further studies were performed for optimizing in vitro culture and biofabrication conditions for 3D bioprinted in vitro skin constructs with pooled five human primary skin cell types (keratinocytes (K), melanocytes (M), dermal fibroblasts (EDF), follicle dermal papilla cells (FDPC), and induced pre-adipocytes (P-Ad/iAd)) seeded with hyaluronan-gelatin based polyethylene glycol (PEG) hydrogels. The total cell number used for printing the epidermis, dermis and hypodermis were 20-30 million/ml, 20-25 million/ml, 10-20 million/ml, respectively. The cell-to-cell ratio for each layer was as following: Epidermis: K:M=5:1, Dermis: HDF:FDPC=4:1, and Hypodermis: P-Ad or iAd. The bioink used for printing consisted of 2 parts (Glycosil): 2 parts (Gelin-S): 1 part (8% (w/v) 4-Arm PEG-Acrylate, MW 5k (PSB-423) from Creative PEGWorks and 10-20% (v/v) 3 mg/ml human collagen solution: VitroCol)). For bioprinting the pressure varied from 40-80 kPa depending on the cell number or density of the Bioink. The printed constructs were cultured in 5% fetal bovine serum containing keratinocyte growth medium for up to 3 weeks and further analyzed for cell distribution and viability.

The results indicated that bioprinting and 3D co-culture of human primary skin cells did not affect the viability of the cells, and the skin constructs maintained their original printed tri-layered structures without much cell migration between printed layers. This study proves the feasibility of developing bioprinted multi-skin cell type based cellular models in vitro.

Fabrication of 3D Biomask for Facial Skin Regeneration

Figure 6:
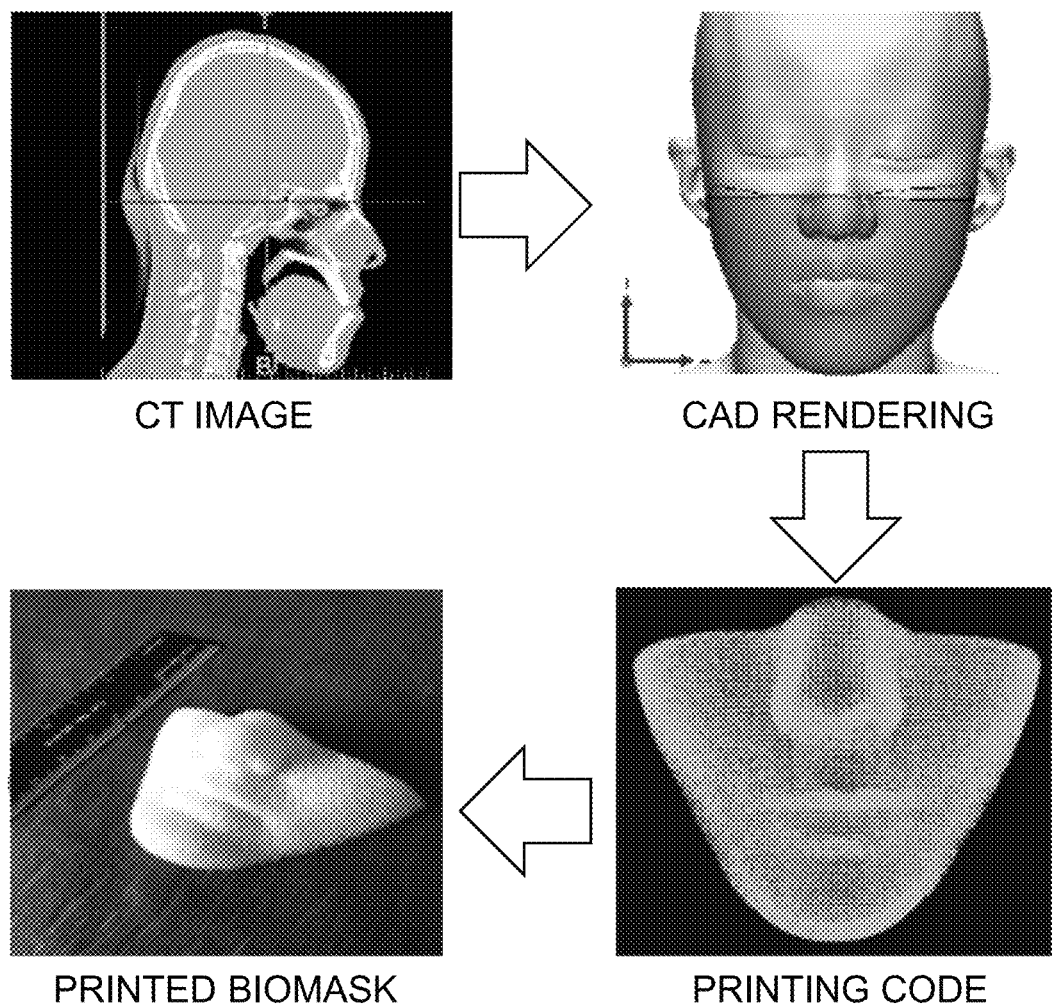
FIG. 6: Data collection and 3D printing of Biomask mold using CAD/CAM modeling.

Burn injury to the face remains one of the greatest challenges in wound care, and treatment may greatly affect the quality of life and social integration of the affected individuals. However, the varied contours and complex movement of the face has been a challenge in repairing the facial wounds. Current treatment strategies following injuries often lead to scarring, infection, graft failure and poor cosmetic outcome. In this study, a customized engineered skin substitute that snuggly fits in to the complex contour, shape and architecture of facial wounds was developed using a 3-D fabricated Biomask (FIG. 6) having a customized face-shaped structure combined with skin cells.

Figure 7:
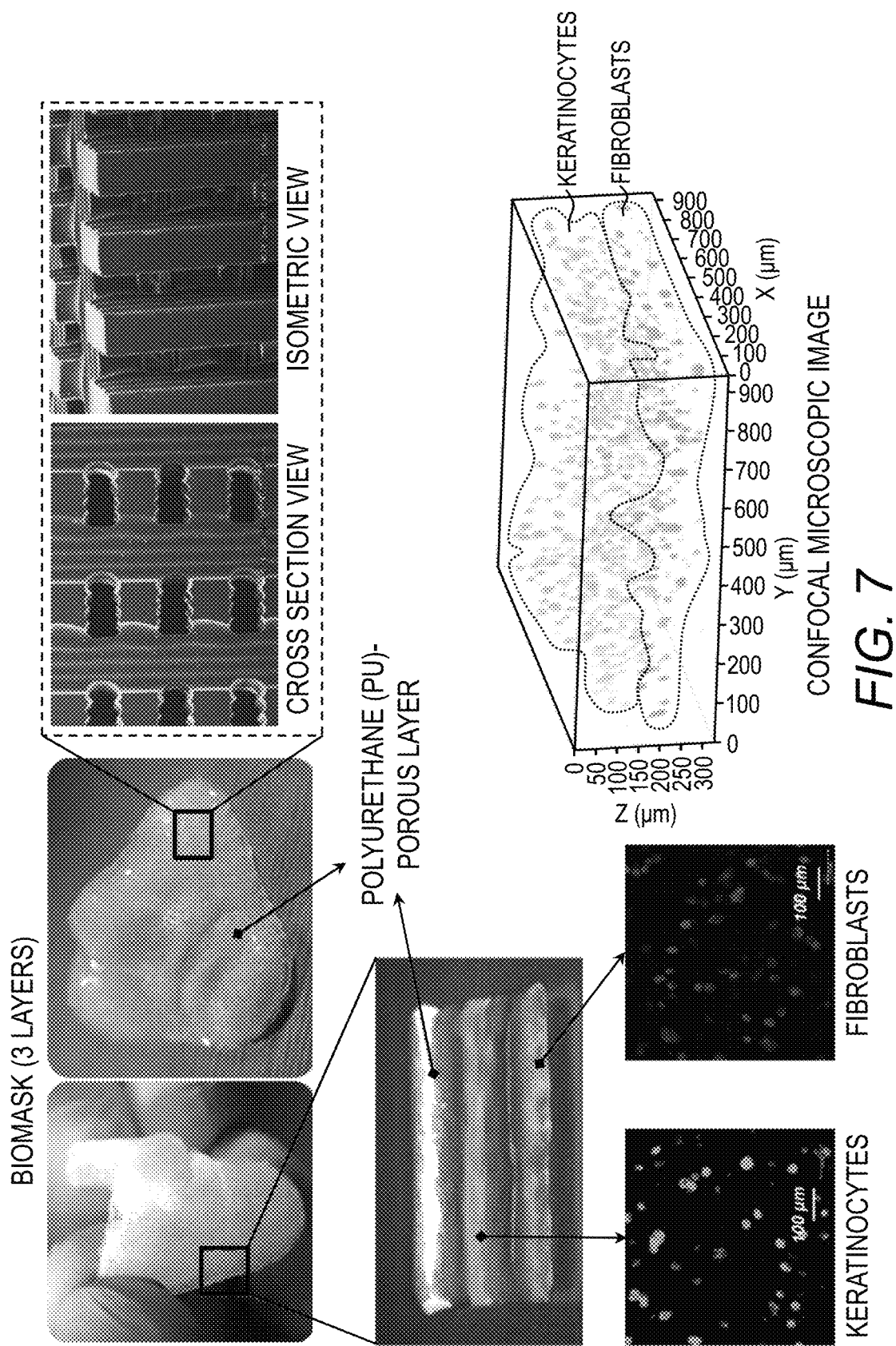
FIG. 7: Views of the porous polyurethane layer, the epidermis-like layer with keratinocytes, and the dermis-like layer with fibroblasts, of the formed Biomask.

An integrated organ printing (IOP) system was used to fabricate the Biomask containing a face-shaped porous polyurethane (PU) with a layer containing human primary keratinocytes and a layer containing human primary dermal fibroblasts (FIG. 7). Each component was precisely dispensed and placed by the control of air pressure and 3-axes stage.

Figure 8:
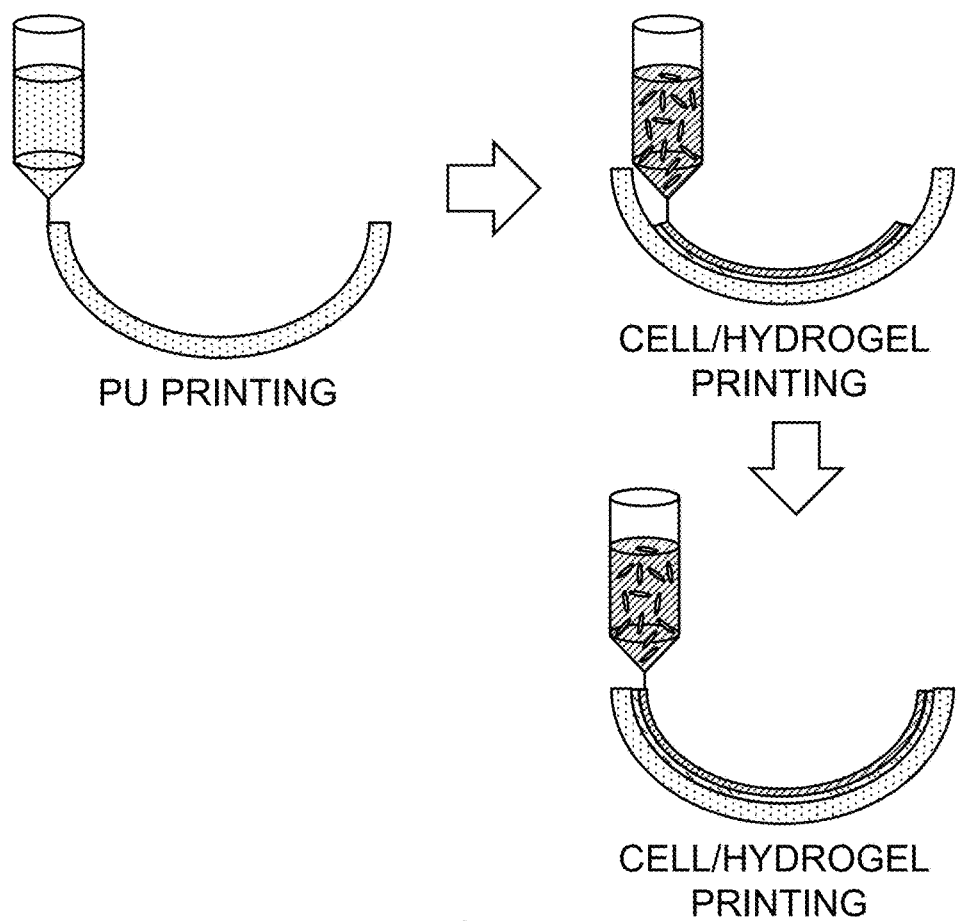
FIG. 8: Schematic of printing each of the layers of the Biomask.
Figure 9:
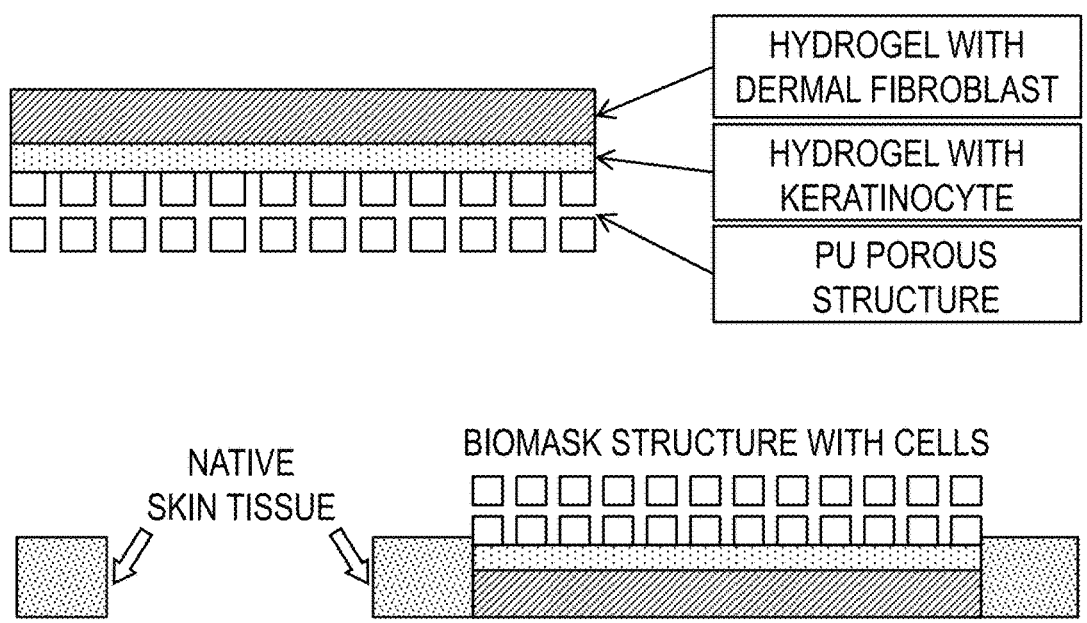
FIG. 9: Schematic design of Biomask structure and in vivo application onto a wound. polyurethane mold is porous (300 μM pore size).

To make the Biomask structure, Polyurethane (PU) was used for the supporting structure. High temperature (around 150 degree-centigrade) and high pressure (1500 kPa) were used for dispensing the PU. A cell/hydrogel mixture for epidermis layer; and then dermis layer, were then printed onto the formed PU structure (FIG. 8). For the epidermis and dermis layers, keratinocytes and fibroblasts were mixed in hydrogel, respectively. As shown in FIG. 9, the PU structure supports the upper hydrogel structure of the epidermis and dermis layers. After implantation, the PU structure can act like a dressing for the skin wound.

The printed constructs were validated in a mouse full-thickness skin wound model. The printed constructs were applied to the full-thickness skin wounds (1×1 cm$^2$) of nu/nu mice. The engineered skin constructs were delivered with the porous PU layer. H&E-stained histological sections of skin samples, harvested at 14 days, showed clear differences in the quality of the epidermal layers near the center of the wound areas between control (nontreated) and engineered skin groups.

The Biomask provides the ability to deliver multiple cell types in a precise manner and maintain customized contours while facilitating rapid wound coverage and closure, which is critical in case of complex facial full-thickness wounds. Clinical use of the Biomask fabricated with the 3-D IOP system is expected to enhance wound healing and skin regeneration and provide personalization to enhance functionality and cosmetic appearance of healed wounds.

The foregoing is illustrative of the present invention, and is not to be construed as limiting thereof. The invention is defined by the following claims, with equivalents of the claims to be included therein.

That which is claimed is:

1. A method of making a skin substitute product, comprising the steps of:
   (a) depositing a first layer comprising live mammalian adipocytes in a first hydrogel carrier on a substrate; then
   (b) depositing a second layer on said first layer, said second layer comprising live mammalian fibroblast cells and live mammalian follicle dermal papilla cells in a second hydrogel carrier; and then
   (c) depositing a third layer on said second layer, said third layer comprising live mammalian keratinocytes and live mammalian melanocytes in a third hydrogel carrier,
   wherein said live mammalian adipocytes are human adipocytes, said live mammalian fibroblast cells are human fibroblast cells, said live mammalian follicle dermal papilla cells are human follicle dermal papilla cells, said live mammalian keratinocytes are human keratinocytes, and said live mammalian melanocytes are human melanocytes.

2. The method of claim 1, wherein:
   said first hydrogel carrier is deposited in prepolymerized or partially polymerized form;
   said second hydrogel carrier is deposited in prepolymerized or partially polymerized form; and/or
   said third hydrogel carrier is deposited in prepolymerized or partially polymerized form.

3. The method of claim 1, wherein:
   said depositing steps (a) and (b) are carried out under conditions in which said first hydrogel in said first layer and said second hydrogel in said second layer at least partially crosslink with one another; and
   said depositing steps (b) and (c) are carried out under conditions in which said second hydrogel in said second layer and said third hydrogel in said third layer at least partially crosslink with one another.

4. The method of claim 1, wherein said depositing steps (a), (b), and/or (c) are carried out by printing.

5. The method of claim 1, wherein said first, second, and/or third hydrogel carriers comprise cross-linked hyaluronic acid.

6. The method of claim 1, wherein:
   (i) said first layer has a thickness of from 100, 200 or 300 micrometers up to 400, 600 or 800 micrometers;
   (ii) said second layer has a thickness of from 100, 200 or 300 micrometers up to 400, 600 or 800 micrometers;
   (iii) said third layer has a thickness of from 100, 200 or 300 micrometers up to 400, 600 or 800 micrometers; and/or
   (iv) said product has a total thickness of 300, 600 or 900 micrometers up to 1200, 1800 or 2400 micrometers.

7. The method of claim 1, wherein each of said first layer, said second layer, and said third layer have overlying surface areas of from 0.5, 1 or 10 square centimeters up to 50, 200 or 400 square centimeters.

8. The method of claim 1, wherein:
   (i) said adipocytes are included in said first hydrogel carrier in an amount of from 1 or 2 million to 8, 10, or 20 million cells per cubic centimeter; and/or
   (ii) said fibroblast cells and said dermal papilla cells are included in said second hydrogel carrier in a ratio of about 8:1 or 6:1 to 2:1 or 1:1 and/or at a combined density of about 5 or 8 million to 15, 20, 25 or 30 million cells per cubic centimeter; and/or
   (iii) said keratinocytes and said melanocytes are included in said third hydrogel carrier in a ratio of about 20:1 or 10:1 to 8:1, 5:1, 3:1 or 2:1 and/or at a combined density of about 5 or 8 million to 15 or 20, 25, 30 or 35 million cells per cubic centimeter.

9. The method of claim 1, further comprising depositing antigen-presenting dendritic cells or precursors thereof between said first layer and said second layer, in said second layer, between said second layer and said third layer, and/or in said third layer.

10. The method of claim 1, further comprising depositing neural cells or precursors thereof between said first layer and said second layer, in said second layer, between said second layer and said third layer, and/or in said third layer.

11. The method of claim 1, further comprising depositing vascular cells or precursors thereof between said first layer and said second layer, in said second layer, between said second layer and said third layer, and/or in said third layer.

12. The method of claim 1, wherein the live mammalian adipocytes are induced pre-adipocytes.

13. The method of claim 5, wherein said second and/or third hydrogel carriers further comprise collagen.

14. A method of making a skin substitute product, comprising the steps of:
  (a) depositing a first layer comprising live mammalian adipocytes in a first hydrogel carrier on a substrate; then
  (b) depositing a second layer on said first layer, said second layer comprising live mammalian fibroblast cells and live mammalian follicle dermal papilla cells in a second hydrogel carrier; and then
  (c) depositing a third layer on said second layer, said third layer comprising live mammalian keratinocytes and live mammalian melanocytes in a third hydrogel carrier,
  said method further comprising depositing antigen-presenting dendritic cells or precursors thereof between said first layer and said second layer, in said second layer, between said second layer and said third layer, and/or in said third layer.

15. The method of claim 14, wherein:
  said first hydrogel carrier is deposited in prepolymerized or partially polymerized form;
  said second hydrogel carrier is deposited in prepolymerized or partially polymerized form; and/or
  said third hydrogel carrier is deposited in prepolymerized or partially polymerized form.

16. The method of claim 14, wherein said depositing steps (a), (b), and/or (c) are carried out by printing.

17. The method of claim 14, wherein:
  (i) said first layer has a thickness of from 100, 200 or 300 micrometers up to 400, 600 or 800 micrometers;
  (ii) said second layer has a thickness of from 100, 200 or 300 micrometers up to 400, 600 or 800 micrometers;
  (iii) said third layer has a thickness of from 100, 200 or 300 micrometers up to 400, 600 or 800 micrometers; and/or
  (iv) said product has a total thickness of 300, 600 or 900 micrometers up to 1200, 1800 or 2400 micrometers.

18. The method of claim 14, wherein:
  (i) said adipocytes are included in said first hydrogel carrier in an amount of from 1 or 2 million to 8, 10, or 20 million cells per cubic centimeter; and/or
  (ii) said fibroblast cells and said dermal papilla cells are included in said second hydrogel carrier in a ratio of about 8:1 or 6:1 to 2:1 or 1:1 and/or at a combined density of about 5 or 8 million to 15, 20, 25 or 30 million cells per cubic centimeter; and/or
  (iii) said keratinocytes and said melanocytes are included in said third hydrogel carrier in a ratio of about 20:1 or 10:1 to 8:1, 5:1, 3:1 or 2:1 and/or at a combined density of about 5 or 8 million to 15 or 20, 25, 30 or 35 million cells per cubic centimeter.

* * * * *